United States Patent [19]

Strow et al.

[11] 4,036,746

[45] July 19, 1977

[54] FLOTATION WITH AMINE-STABILIZED DIALKYL DITHIOPHOSPHATES

[75] Inventors: Lawrence Evans Strow; Franklin Anderson Bolth, both of Baltimore, Md.

[73] Assignee: Minerec Corporation, New York, N.Y.

[21] Appl. No.: 669,256

[22] Filed: Mar. 22, 1976

Related U.S. Application Data

[62] Division of Ser. No. 497,905, Aug. 16, 1974, Pat. No. 3,971,836.

[51] Int. Cl.² ............................................. B03D 1/02
[52] U.S. Cl. ........................................ 209/166; 252/61
[58] Field of Search ................. 209/166, 167; 252/61; 260/925

[56] References Cited

U.S. PATENT DOCUMENTS

| | | | |
|---|---|---|---|
| 2,063,629 | 12/1936 | Sulzberg | 260/925 X |
| 2,193,965 | 3/1940 | Huckwalt | 260/925 X |
| 2,206,284 | 7/1940 | Jayne | 209/166 X |
| 2,409,344 | 10/1946 | Davis | 260/925 X |
| 2,930,730 | 3/1960 | Scott | 260/925 X |
| 3,002,014 | 9/1961 | Dinsmore | 260/925 X |
| 3,074,990 | 1/1963 | Cyba | 260/925 |
| 3,317,040 | 5/1967 | Booth | 252/61 X |
| 3,662,034 | 5/1972 | Oswald | 260/925 X |

*Primary Examiner*—Robert Halper
*Attorney, Agent, or Firm*—James J. Burke

[57] ABSTRACT

The quality of dialkyl dithiophosphates as flotation promoters is improved by addition to the neutralized acid of small quantities of a trialkyl amine. More important, promoters thus stabilized exhibit markedly increased storage life and substantially no tendency to corrode steel. Shipping and storage of these products is thus facilitated.

3 Claims, No Drawings

FLOTATION WITH AMINE-STABILIZED DIALKYL DITHIOPHOSPHATES

RELATED APPLICATIONS

This application is a division of application Ser. No. 497,905, filed Aug. 16, 1974, now U.S. Pat. No. 3,971,836, issued July 27, 1976.

BACKGROUND OF THE INVENTION

The present invention relates in general to dithiophosphates and, more particularly, it relates to dialkyl dithiophosphates which have a long-established utility as promoters or collectors in the beneficiation of mineral-bearing ores by flotation, most particularly copper ores.

Dialkyl dithiophosphates are defined by the following general formula:

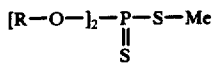

where R is an alkyl group generally having less than 6 carbon atoms, and Me is any suitable dissociating cation such as sodium potassium, calcium or the like. These compounds are produced by reacting phosphorus pentasulfide with aliphatic alcohols.

The compounds can be used in a variety of forms. Concentrated aqueous solutions of ammonium salts of dialkyl dithiophosphoric acids may be used, but these are unstable even with excess ammonium hydroxide, and decompose into the free acid and gaseous decomposition products in a short period. Neutral salts of alkyl diesters of dithiophosphoric acid have also been used, and while not corrosive, they are hard-to-dry gels or pastes that, once dry, are difficult to dissolve. A further approach was to neutralize the alkyl diesters with an alkali metal base, and heat the mixture with a large excess of the base to obtain a stable, dry solid, but this reduces the concentration of active ingredient and raises cost with no improvement in performance. Also, if the base is an alkaline carbonate this can cause precipitates to form in hard water, which hinders the flotation. Lastly, it has been proposed to provide an aqueous solution including a neutralized dithiophosphoric acid (or its hydrolysis product) with an excess of alkali metal base amounting to 10-25%.

These solutions are preferable to the pasty mixes including excess sodium carbonate, but stability for more than six months is questionable.

Early references to these compounds and their use as flotation promoters may be found in U.S. Pat. Nos. 1,593,232 and 2,038,400. Ammonium salt solutions of the compounds are disclosed in U.S. Pat. No. 2,206,284. Hydrolyzed compounds are disclosed in U.S. Pat. No. 2,919,025. The compounds stabilized with 10-25% excess alkali are disclosed in U.S. Pat. No. 3,086,653, and, most recently, certain specific branched-chain dithiophosphates are disclosed in U.S. Pat. No. 3,570,772.

It is believed that in systems containing 10-25% excess caustic, the excess caustic is slowly continuing to hydrolize the alkyl radicals from the phosphorus atom to form sodium phosphates, and there is a slow deterioration. Any solution of a salt of dialkyl dithiophosphate that obtains a pH of 6 or below becomes extremely corrosive and over several weeks forms polymers, hydrogen sulfide and other products of decomposition. For example, solutions of di-isobutyl dithiophosphate having a 20-25% excess of sodium hydroxide are observed to deposit a black, varnish-like sludge slowly with time. It is believed that the principle corrosive agent is the =P:SSH ion which attacks steel very rapidly. Since the only practical containers for the storage and shipping of these solutions are cold-rolled steel drums, this becomes an unsatisfactory approach. Further, the use of substantial excess caustic makes the solution dangerous to handle.

OBJECTS OF THE INVENTION

A general object of the present invention is to provide dialkyl dithiophosphate solutions of improved operability and stability.

Another object of the present invention is to provide dialkyl dithiophosphates in a form that is not corrosive to steel over extended periods (i.e. years).

A further object of the present invention is to provide dialkyl dithiophosphate promoters having improved flotation characteristics.

A still further object of the present invention is to avoid decomposition of dialkyl dithiophosphate solutions with time.

A still further object of the present invention is to provide dialkyl dithiophosphate promoters in a form suitable for world-wide shipping in steel drums without any "shelf life" restrictions.

A still more specific object of the present invention is to provide a strong aqueous solution of sodium diisobutyl dithiophosphate that remains stable in the presence of cold rolled steel for an indefinitely long time and is not corrosive of the metal.

Various other objects and advantages of the invention will become clear from the following description of embodiments and specific examples thereof, and the novel features will be particularly pointed out in connection with the appended claims.

DESCRIPTION OF EMBODIMENTS

Understanding of the present invention will be facilitated by first considering the behavior of di-isobutyl dithiophosphates neutralized with varying amounts of caustic over periods of time.

It has been determined that if little or no excess caustic is used in such neutralizations, solutions resulted that were corrosive or cold rolled steel as time passed. This statement is based upon observations of the behavior of several solutions during storage in glass at 90° F. and above. Some of the samples contained pieces of cold rolled steel, and others did not. The di-isobutyl dithiophosphoric acid used had an 85% sodium hydroxide value, according to the manufacturer.

In one instance the dithio acid was neutralized with the stoichiometric amount of caustic (50%). The solution that resulted had a pH of 6. Small increments of caustic were added to the solution with stirring until 102.5% of the calculated amount of caustics was used. That solution remained alkaline over a week-end (pH=7.3). Use of lesser amounts of caustic between 100% and 102.5% of the calculated amount resulted in solutions whose pH could be seen to migrate during brief periods of observation.

Another 50% solution was prepared using 103.7% of the calculated amount of caustic. Its original pH was about 11, according to test paper. After 34 days of standing in glass at room temperature the solution pH was 8-9, again according to test paper. A weighed sample of cold rolled steel and a 50 day old sample of this dithio acid solution were kept together in a stoppered flask for 66 days. During that time the metal lost 2.04% of its original weight and the solution's pH migrated to 7.45.

A 50% solution that was prepared by neutralizing the same parent acid with 105% of the calculated amount of caustic underwent a pH change from 11.1 to 9.2 during approximately 3 years of storage at 90° F. and above, in contact with a sample of cold rolled steel. The metal sample lost 5.12% of its weight at the same time. Another solution that was prepared by neutralizing the parent acid with 105% of the calculated amount of caustic and contained added methyl isobutyl carbinol (hereafter "mibc") to the extent of 5% of its gross weight acted similarly during approximately 3 years storage at 90° F. and above. The pH of the solution migrated from 11.35 to 9.60 and a sample of cold rolled steel that was immersed in the solution lost 9.4% of its original weight. The use of mibc or related compounds is widely practiced for frothing purposes in flotation.

Sodium di-isobutyl dithiophosphate solution was manufactured by reaction of phosphorus pentasulfide and isobutyl alcohol according to known techniques. To it was added 5% mibc and 109% of the calculated amount of caustic to neutralize the parent acid. During approximately 3 years of standing in glass at 90° F. and above the solution's pH remained virtually constant. A weighed sample of cold rolled steel that was immersed in the solution for that period of time, however, lost 13.05% of its original weight.

A 50% aqueous sodium di-isobutyl dithiophosphate solution that was prepared by combining the parent acid with 125% of the calculated amount of caustic was found to gradually release from solution a trace of resinous appearing material plus other solid trash, while at the same time the supernatant liquid remained clear and alkaline.

A 50% aqueous sodium di-isobutyl dithiophosphate solution prepared using only 105.8% of the calculated amount of caustic and no mibc exhibited evidence of instability in a brief period of days. A solution that had a pH=9 when freshly made had a pH = 7.3-7.5 after only a few days of standing. About 1.6% of this mixture's volume was an insoluble oil (ester).

A 50% aqueous sodium di-isobutyl dithiophosphate solution that was prepared by using 107.3% of the calculated amount of caustic exhibited the same suggestion of instability as did solutions made with 105.8% of the calculated amount of caustic, in that the solutions pH migrated from about 11 to 8-9 fifteen days later. This solution had a specific gravity at 15.5° C. = 1.106 and a freeze point = −5° C. It was found to consist of 2 layers of liquid — the lighter layer having a volume equal to 1.6% of the mixture's total volume.

Thus, it is to be appreciated that when these solutions are neutralized with only 5% excess caustic or 10-25% as taught in the prior art, long-term stability and corrosion are still significant problems.

In essence, the present invention is based on our discovery that all of the above-noted problems can be overcome if the solution is neutralized with just the amount of caustic that is sufficient to remove all initial acidity (a 5% excess is typical), and there is added thereto a small quantity (2.5-5%) of a trialkyl amine. While not wishing to be bound to any particular theory of operation, it is believed that these amines are sufficiently alkaline to react with any acids that are formed, but are not strong enough to attack the dithiophosphate compounds.

The procedure to test the stability of these mixtures, the results of which are reported hereinbelow in the Examples, was as follows.

Fifty percent aqueous solutions of sodium di-isobutyl dithiophosphate (hereafter "Na.Db.Dt.P") were prepared and their pH determined. A portion of each solution was innoculated with the compound being tested and another portion was not. In each sample there was placed a weighed piece of cold rolled steel straping metal. Finally, the flasks containing the tests were tightly stoppered and stored for long periods of time at 90° F. and above. Prior to the start of some of these tests the Na.Db.Dt.P solutions were filtered so that solids found in the flasks at the end of the tests could be said to have formed as the solutions aged. After a period of standing the pH of each solution was measured again, its physical appearance noted and the metal sample was examined and weighed. Continued clarity of the solution, a pH near its original value and the absence of weight loss by the metal sample were taken to be indications of the effectiveness of a material.

EXAMPLE I

The trial of trimethyl amine was started on May 21, 1971 and ended on February 28, 1974. In the test a 50% Na.Db.Dt.P solution that had been prepared using 105% of the stoichiometric amount of caustic to neutralize the parent acid was used. It was filtered prior to the addition of the amine to it. The amount of 25% aqueous trimethyl amine used in the solution was such that the anhydrous amine present constituted 2.3% by weight of the final mixture. The composition of the test solution is described in more detail as follows:

TABLE I

| Water | 46.4% by Weight |
|---|---|
| Sodium Db . Dt . P | 40.3% by Weight |
| Ester and alcohol | 6.1% by Weight |
| Mibc | 4.5% by Weight |
| Excess Caustic | 0.3% by Weight |
| Trimethyl Amine | 2.3% by Weight |

When the test was concluded the solution was a transparent, pale yellow liquid that was clear of dirt. The metal sample was still in its original bright state. There was an apparent weight gain by metal sample of 0.0024g., or about 0.07%.

EXAMPLE II

The trial of triethyl amine was started on May 3, 1971 and concluded on Feb. 28, 1974. A 50% Na.Db.Dt.P solution was used that was derived from the neutralization of the parent acid with 105% of the stoichiometric amount of caustic. The salt solution was filtered before Mibc and amine were added to it. The amount of triethyl amine used was such that the final reagent had the following composition:

TABLE II

| Water | 42.4% by Weight |
|---|---|
| Sodium Db . Dt . P | 43.3% by Weight |
| Ester and alcohol | 6.6% by Weight |
| Mibc | 4.9% by Weight |
| Excess Caustic | 0.3% by Weight |
| Triethyl amine | 2.5% by Weight |

The appearances of both the metal sample and the supernatant liquid were unchanged during the testing interval. The solution pH started at 11.08 and was 11.35 at the end. There was an apparent weight gain by metal sample of 0.0005g. or 0.01%.

EXAMPLE III

A third test was run as a control. In it the 50% sodium Db.Dt.P solution used was the identical solution used in the triethyl amine test except that no amine was added to it. The parent acid was neutralized with 105% of the calculated amount of caustic and the resulting solution was filtered prior to starting the test. The test was run from May 5, 1971 until Feb. 28, 1974. At the end of the test the supernatant liquid was a viscous, black syrup. The metal sample was thickly encrusted with black solids. After a thorough cleaning by scrubbing with soapy steel wool the metal sample was found to be deeply etched and pitted. During the test, the pH went from 11.1 to 9.2, and the loss of weight by the metal sample was 0.2798g. or 5.12%.

Examples I-III demonstrates two things: (1) That 50% Na.Db.Dt.P solutions that have been prepared by neutralizing the parent acid with 105% of the stoichiometric amount of caustic decompose in contact with cold rolled steel as time passes and are corrosive of the metal. Thus if long-term storage of Na.Db.Dt.P solutions in steel drums is desired the amines must be incorporated into them. (2) Trimethyl and triethyl amines serve well for 50% Na Db Dt P solutions that are in contact with cold rolled steel. While amine additions of about 2.5% are preferred for the conditions noted, additions in the range of 0.5 to 5% will provide benefits; if amine additions are in the low end of this range, a somewhat greater excess of caustic will improve results.

EXAMPLE IV

Utility of the invention was established with other dialkyl dithiophosphates. In particular, aqueous solutions of di-isopropyl dithiophosphate, di-n-butyl dithiophosphate, and di-primary amyl dithiophosphate were likewise stabilized by the incorporation of trialkyl amines. It was further established that the invention was not operable with the lower alkyls, methyl and ethyl, so the present invention is considered operable with alkyls having 3-6 carbon atoms.

EXAMPLE V

In the following examples, comminuted copper sulfide ores were subjected to separate froth flotation operations in the presence of the products of Examples I-III but otherwise under substantially identical conditions, the results of which are shown in Table III.

TABLE III

| Ore No. 1 Assaying .567% Cu | | |
|---|---|---|
| | Copper Concentrate, % Cu | |
| | Assay | Recovery |
| Product of Example I | 13.06 | 82.36 |
| Product of Example II | 12.79 | 82.36 |
| Product of Example III | 12.43 | 81.31 |
| Ore No. 2 Assaying .721Ft Cu | | |
| | Copper Concentrate % Cu | |
| | Assay | Recovery |
| Product of Example I | 12.44 | 81.41 |
| Product of Example II | 12.91 | 81.28 |
| Product of Example III | 13.85 | 79.89 |

In addition to the indicated deterioration of the recovery with the unstabilized product of Example III, the results of continuous, large-scale operations are further impaired by erratic operation due to accumulated debris in the reagent feeding system.

Various changes in the details, steps, materials and arrangements of parts, which have been herein described and illustrated in order to explain the nature of the invention, may be made by those skilled in the art within the principle and scope of the invention as defined in the appended claims.

What is claimed is:

1. In the flotation of finely divided copper sulfide ores for the recovery of contained mineral values, the improvement comprising utilizing as a promoter therein a neutralized storage-stable mixture of:

an aqueous solution of a dialkyl dithiophosphate having the general formula

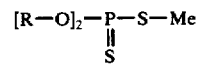

where R is an alkyl group having 3 to 6 carbon atoms and Me is a dissociating cation; said solution being neutralized with sufficient caustic to remove all initial acidity and 0.5 to 5% by weight of a trialkyl amine.

2. The flotation as claimed in claim 1, wherein said dithiophosphate is selected from the group consisting of di-isobutyl dithiophosphate, di-isopropyl dithiophosphate, di-n-butyl dithiophosphate and di-primary amyl dithiophosphate.

3. The flotation as claimed in claim 1, wherein said amine is selected from the group consisting of trimethyl amine and triethyl amine.

* * * * *